(12) United States Patent
Rathjen

(10) Patent No.: US 8,746,881 B2
(45) Date of Patent: Jun. 10, 2014

(54) DEVICE FOR PROCESSING EYE TISSUE BY A MEANS OF FEMTOSECOND LASER PULSES

(75) Inventor: Christian Rathjen, Bremen (DE)

(73) Assignee: SIE AG, Surgical Instrument Engineering (CH)

( * ) Notice: Subject to any disclaimer, the term of this patent is extended or adjusted under 35 U.S.C. 154(b) by 298 days.

(21) Appl. No.: 13/191,752

(22) Filed: Jul. 27, 2011

(65) Prior Publication Data

US 2012/0029491 A1 Feb. 2, 2012

Related U.S. Application Data

(60) Provisional application No. 61/368,724, filed on Jul. 29, 2010.

(51) Int. Cl.
*A61B 3/10* (2006.01)
(52) U.S. Cl.
USPC ............ 351/205; 351/208; 351/213; 351/214
(58) Field of Classification Search
USPC .................................................. 351/205, 221
See application file for complete search history.

(56) References Cited

U.S. PATENT DOCUMENTS

| | | | |
|---|---|---|---|
| 6,882,462 B2 * | 4/2005 | Helsel et al. .................. | 359/292 |
| 7,621,637 B2 | 11/2009 | Rathjen et al. | |
| 2007/0010804 A1 * | 1/2007 | Rathjen et al. .................... | 606/5 |
| 2007/0106285 A1 | 5/2007 | Raksi | |
| 2010/0305553 A1 * | 12/2010 | Kittelmann et al. .............. | 606/4 |
| 2013/0128228 A1 * | 5/2013 | Zhou et al. .................... | 351/214 |

FOREIGN PATENT DOCUMENTS

| | | |
|---|---|---|
| EP | 0176872 | 9/1985 |
| EP | 0615721 | 9/1994 |
| EP | 1 731 120 A1 | 12/2006 |
| JP | 10-328198 | 12/1998 |
| JP | 2006-341103 | 12/2006 |

OTHER PUBLICATIONS

English translation of Japanese Notification of Reasons for Refusal dated Mar. 4, 2014 for corresponding Japanese Patent Application No. 2011-165505 (6 pages).

* cited by examiner

*Primary Examiner* — Jordan Schwartz
(74) *Attorney, Agent, or Firm* — Ostrolenk Faber LLP

(57) ABSTRACT

For processing eye tissue (8) by means of femtosecond laser pulses, an ophthalmological device (1) includes a projection optical unit (2) for the focused projection of the femtosecond laser pulses into the eye tissue (8). Disposed upstream of the projection optical unit (2) is a first beam-deflecting scanner system (3) for scanning the eye tissue (8) with the femtosecond laser pulses along a processing line. A second beam-deflecting scanner system (5) is disposed upstream of the first scanner system (3) and is designed for scanning the eye tissue (8) with the femtosecond laser pulses in a scanning movement superimposed on the processing line and running in a deflection plane. The second scanner system (5) has a scanner speed that is a multiple of the scanning speed of the first scanner system (3). A rotation system is provided for aligning the deflection plane with a defined angle with respect to the processing line.

18 Claims, 3 Drawing Sheets

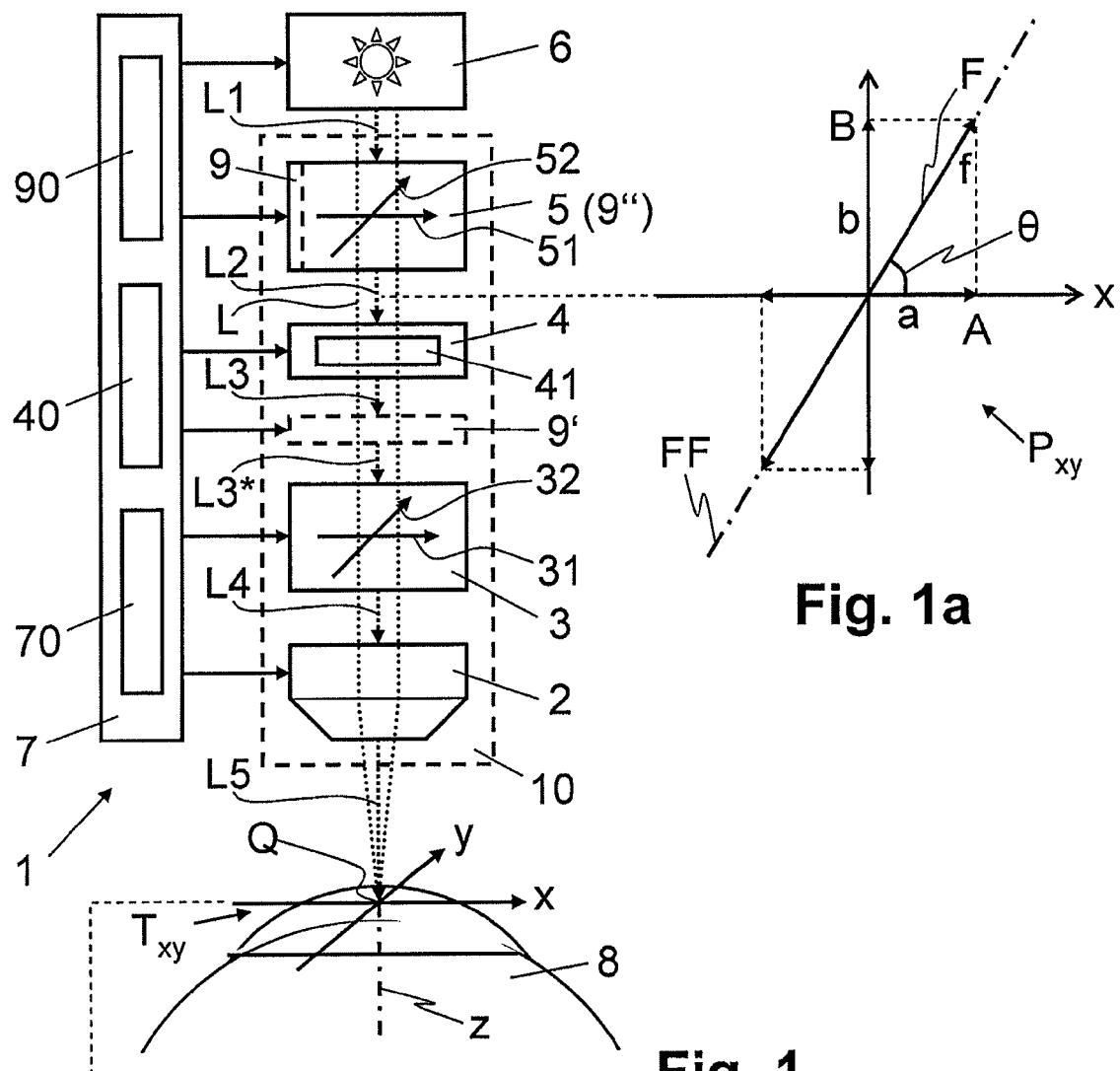
Fig. 1a
Fig. 1
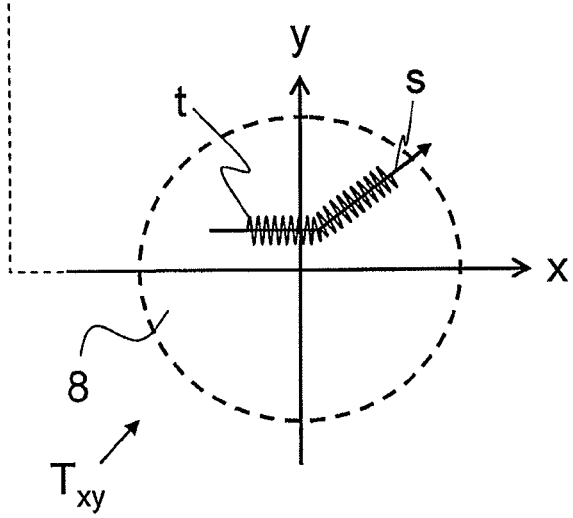
Fig. 1b

DEVICE FOR PROCESSING EYE TISSUE BY A MEANS OF FEMTOSECOND LASER PULSES

CROSS REFERENCE TO RELATED APPLICATIONS

The present application claims benefit of and priority to U.S. Provisional Patent Application Ser. No. 61/368,724 filed Jul. 29, 2010 entitled VORRICHTUNG ZUM BEARBEITEN VON AUGENGEWEBE MITTELS FEMTOSEKUNDENLASERPULSEN, the entire contents of which are hereby incorporated by reference herein.

BACKGROUND

1. Field of the Disclosure

The present invention relates to an ophthalmological device for processing eye tissue by means of femtosecond laser pulses. The present invention relates, in particular, to an ophthalmological device including a projection optical unit for the focused projection of the femtosecond laser pulses into the eye tissue.

2. Related Art

For processing eye tissue by means of laser beams, an image region or a working region is scanned with laser pulses by means of the pulsed laser beam being deflected in one or two scanning directions by means of suitable scanner systems (deflection devices). The deflection of the light beams or of the laser pulses, for example femtosecond laser pulses, is generally performed by means of movable mirrors which are pivotable about one or two scanning axes, for example by means of galvanoscanners, piezoscanners or polygon scanners.

U.S. Pat. No. 7,621,637 describes a device for processing eye tissue, said device having a base station with a laser source for generating laser pulses and a scanner arranged in the base station with movable deflection mirrors for deflecting the laser pulses in a scanning direction. The deflected laser pulses are transmitted via an optical transmission system from the base station to an application head, which moves over a working region in accordance with a scanning pattern by means of a mechanically moved light projector. The deflection in the scanning direction, which is much faster compared with the mechanical movement, is superimposed in the application head onto the mechanical movement of the light projection and thus onto the scanning pattern thereof. A fast scanner system in the base station enables a fine movement of the laser pulses (microscan), which is superimposed onto the scanning pattern of the movable light projector that covers a large working region, for example the entire eye.

With the availability of faster laser pulses that yield ever higher pulse rates, for example more than one million pulses per second (MHz), the known scanner systems encounter their physical limits of being able to position pulses separately, and the pulse rate of the lasers has to be artificially reduced. In particular, the mechanical movement of light projectors or lenses for scanning working regions, and also the mass inertia of galvanometer scanner systems, which does not permit arbitrarily high accelerations, limit the possible scanning patterns and scanning trajectories to the effect that greater changes in direction have to be avoided, and that the pulse rate has to be actively reduced (in a complicated manner) or the laser has to be switched off when the minimum scanning speed is undershot, for example at reversal points. Consequently, the known scanner systems impose significant limits on cut guidances that can be implemented. From a clinical standpoint, however, it is desired to plan the cut profile according to the biomechanical behaviour of the tissue, and not necessarily according to the speed and bandwidth of the scanner system, as is carried out with the known scanner systems. In contrast to surface processing, when cutting soft tissue, for example eye tissue, it is not always possible to employ simple pulse scanning patterns, for example line or spiral patterns, since tissue deformations can be caused by internal evolution of gas or release of stresses, and it is necessary to avoid said tissue deformations by means of suitably more complex scanning patterns taking account of the expected biomechanical behaviour of the tissue. Although the known scanner systems make it possible to process simple scanning patterns, for example to cut a tissue flap, this generally being performed as a large area segment with a simple edge geometry, in the case of isolated processing regions with a complicated edge geometry, such as are required for refractive correction, for example, or in the case of other, biomechanically governed more complex scanning patterns, that is no longer possible in such a simple manner. By way of example, it is then necessary for a large-area scanning pattern to be covered with a mask (electronically or optically), or the small regions are processed, e.g. scanned, individually, which results in a corresponding reduction of the processing speed, since the scanner system has to decelerate and accelerate very frequently relative to the section to be scanned.

SUMMARY

It is an object of the present invention to propose an ophthalmological device for processing eye tissue by means of femtosecond laser pulses which does not have at least some disadvantages of the known systems. In particular, it is an object of the present invention to propose an ophthalmological device for processing eye tissue by means of femtosecond laser pulses which manages without mechanical movement of lenses for the scanning of a processing region and allows the use of laser sources having high pulse frequencies, in particular pulse frequencies in the MHz range with more than one million pulses per second in order to reduce the processing time, and a more flexible cut guidance.

The aims mentioned above are achieved by the present invention in particular by virtue of the fact that an ophthalmological device for processing eye tissue, in particular over the entire eye, by means of femtosecond laser pulses, which includes a projection optical unit for the focused projection of the femtosecond laser pulses into the eye tissue, is additionally provided with a first beam-deflecting scanner system disposed upstream of the projection optical unit, for scanning the eye tissue with the femtosecond laser pulses along a processing line, a second beam-deflecting scanner system disposed upstream of the first scanner system, for scanning the eye tissue with the femtosecond laser pulses in a scanning movement superimposed on the processing line and running in a deflection plane, and a rotation system for aligning the deflection plane with a defined angle with respect to the processing line.

For practical apparatus reasons and for cost reasons it is necessary to limit the size (e.g. the diameter) of the projection and transmission optical units in such a way that, in general, excursion or scanning angles of significantly less than 90 degrees can expediently be realized. In the case of a very small focus of the laser pulses (spots) such as are required for tissue-protective and precise processing, for example spots having a diameter of less than 5 μm, in particular less than 3 μm, preferably less than 1 μm, and a large image field (processing region), therefore, large beam diameters have to be scanned, which necessitates large and heavy mirrors and thus, as in the case of solutions with mechanically moved lenses, low scanning frequencies. In other words: for fundamental physical reasons, large image fields cannot be scanned with small (i.e. rapidly deflectable) mirrors and at the same time have spot diameters that are desirably small for the processing quality.

The cascading of the two beam-deflecting scanner systems with movable deflection mirrors enables eye tissue to be processed in a flexibly configurable and controllable manner, wherein the first scanner system covers an extended processing region, for example the entire eye, and the second scanner system disposed upstream superimposes a fast fine scanning movement, the form, size and orientation of which are flexibly adjustable, without overly large projection and transmission optical units having to be used, and without a mechanical movement of lenses or projection objectives being required for scanning, with the result that high scanning frequencies or scanning rates can be realized. The arrangement of the comparatively faster second scanner system, the "ultrafast scanner system", between the laser source and the first scanner system, the "fast main scanner system", allows the use of smaller beam apertures, e.g. mirrors, and thus enables fast, high-frequency scanning of the eye tissue. In this case, the faster second scanner system can be optimized for high-frequency scanning and processing, i.e. cutting, of the eye tissue with a relatively small excursion, and the first scanner system can be optimized for rapidly moving to any addressable points in the extended processing region (image region). By virtue of the automatic alignment of the deflection plane and hence of the fine scanning movement of the ultrafast scanner system with respect to the processing line of the main scanner system, for example perpendicularly or at some other defined angle, complex cuts are made possible which are not limited to raster-type scanning patterns.

Preferably, the first scanner system has two scanning axes aligned orthogonally with respect to one another for deflecting the femtosecond laser pulses, the second scanner system is designed to deflect the femtosecond laser pulses with a scanning speed that is a multiple of the scanning speed of the first scanner system, and the rotation system is disposed upstream of the first scanner system.

In the case of mirror-based scanner systems, the term scanning axis should be understood as equivalent to the mirror axis, such that a deflection of the mirror about the scanning axis brings about a deflection of a laser beam in a scanning direction running in the deflection plane. In the case of other scanner systems not having a mirror axis, the term scanning axis should be understood as a virtual axis about which a mirror would have to be rotated in order to deflect the laser beam in the relevant scanning direction.

Preferably, the rotation system includes a rotation module and a rotation control module, wherein the rotation module is designed to perform a defined rotation of the deflection plane about an optical projection axis, and wherein the rotation control module is designed to define the rotation of the deflection plane on the basis of the course of the processing line.

Depending on the embodiment variant, the rotation module includes a rotation element configured from mirrors, a rotation element configured from prisms, and/or a drive module coupled to the second scanner system and designed to rotate the second scanner system about the optical projection axis.

In one embodiment variant, the second scanner system has two scanning axes aligned orthogonally with respect to one another for deflecting the femtosecond laser pulses, and the rotation control module is designed to determine the alignment of the scanning movement running in the deflection plane with respect to the processing line by coupled control of the excursion amplitude of the deflection about the first scanning axis and of the excursion amplitude of the deflection about the second scanning axis. As a result of the simple control of the alignment of the scanning movement on the basis of the excursion amplitudes, a costly and slow mechanical and/or optical image rotator becomes invalid, since the control is effected entirely by electronic and/or programming means.

In one embodiment variant, the device includes a scanning control module, which is designed to control the width of the scanning movement of the second scanner system depending on the directional course of the processing line and/or on the current scanning speed of the first scanner system. By way of example, the width of the scanning movement is increased in the case of a slow advancing speed in the direction of the processing line, in order thereby to increase the distance between individual projected femtosecond laser pulses or to reduce the number of femtosecond laser pulses within a defined scanning width. The scanning control module is therefore designed to control the width of the scanning movement of the second scanner system in such a way that the distance between two successive femtosecond laser pulses and the number of femtosecond laser pulses in a defined transmission region are variable.

In a further embodiment variant, a diaphragm is arranged between the first scanner system and the second scanner system and serves for masking out femtosecond laser pulses that are deflected by the upstream second scanner system into a region outside a defined transmission region or a defined scanning width.

In a further embodiment variant, the diaphragm has a controllable, variable diaphragm region or transmission region.

In one embodiment variant, the device includes a diaphragm control module, which is designed to control the size of the variable diaphragm region or transmission region depending on the scanning speed of the first scanner system.

Preferably, the diaphragm is configured as a field stop.

Preferably, the first scanner system has a significantly greater degree of excursion in comparison with the second scanner system.

In one embodiment variant, the two scanning axes of the first scanner system that are aligned orthogonally with respect to one another are coupled to a common deflection mirror.

In one embodiment variant, the second scanner system is designed to scan the eye tissue with the femtosecond laser pulses in an oscillating scanning movement.

In one embodiment variant, the device includes a controllable filter module for selectively excluding femtosecond laser pulses in a defined region of the superimposed scanning movement.

BRIEF DESCRIPTION OF THE DRAWINGS

An embodiment of the present invention is described below on the basis of an example. The example of the embodiment is illustrated by the following enclosed figures:

FIG. 1: shows a block diagram schematically illustrating an ophthalmological device including two cascaded scanner systems and a rotation system for processing eye tissue by means of femtosecond laser pulses.

FIG. 1a: schematically shows in a projection plane the superimposition of scanning movements about two mirror or scanning axes arranged orthogonally with respect to one another, said scanning movements oscillating in a manner that is not phase shifted.

FIG. 1b: schematically shows a processing plane with a scanning trajectory resulting from the cascading of the scanner systems.

DETAILED DESCRIPTION OF THE EMBODIMENTS

Figure 2:
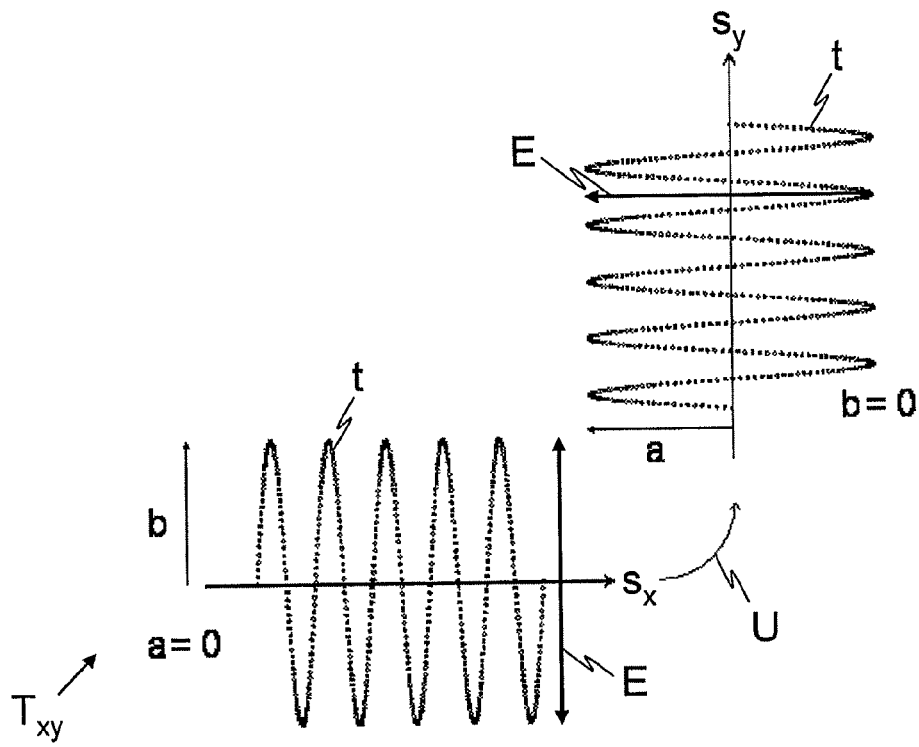
FIG. 2: illustrates the superimposition of a scanning movement of a scanner system onto the processing line of a further scanner system, wherein, in the case of a change in the direction of the processing line, the alignment of the scanning movement with respect to the processing line is automatically adapted.

In FIG. 1, the reference symbol 1 refers to an ophthalmological device for processing eye tissue 8 by means of a pulsed laser beam L1 with femtosecond laser pulses. The pulsed laser beam L1, preferably having pulse frequencies in the MHz range with more than one million pulses per second, is supplied by a beam source 6 and, in a manner focused by means of an optical transmission system 10, projected along a scanning trajectory t as a pulsed processing beam L5 onto or into the eye tissue 8. Depending on the embodiment, the beam source 6 is part of the optical transmission system 10 or configured as a separate unit connected to the optical transmission system 10 via a light transmission system, for example a fibre-optic line and/or a mirror/lens system.

As is illustrated schematically in FIG. 1, the ophthalmological device 1 or the optical transmission system 10 includes two beam-deflecting scanner systems 3, 5 and an optional filter module 4, which are arranged in the beam path (L1-L2-L3-L3*-L4) from the beam source 6 to the projection optical unit 2.

The beam-deflecting scanner system 5 has a scanning speed that is a multiple of the scanning speed of the scanner system 3. Accordingly, in the following description, the scanner system 5 is designated as fast scanner system 5 and the scanner system 3 as slow scanner system 3. Consequently, the fast scanner system 5 has a deflection speed that is faster by a multiple, and, in the case of oscillating scanner systems, oscillation frequencies ($\omega_x$, $\omega_y$) that are higher by a multiple relative to what would be feasible with the slow scanner system 3. In particular, the fast scanner system 5 has a higher scanning speed in the image field of the projection objective (cutting objective), that is to say in the image field of the projection optical unit 2, and/or has a higher scanning frequency. On the other hand, the slow scanner system 3 has a significantly greater degree of excursion in the image field of the projection optical unit in comparison with the fast scanner system 5. Consequently, the slow scanner system 3 makes it possible to cover and address a much larger image field and processing region in comparison with the fast scanner system 5, such that the eye tissue 8 can be scanned completely over the entire eye and be processed with femtosecond laser pulses.

The fast scanner system 5 is preferably arranged between the beam source 6 and the slow scanner system 3. The fast scanner system 5 is arranged for example in the beam path directly downstream of the beam source 6.

The slow scanner system 3 is preferably arranged between the fast scanner system 5 and the projection optical unit 2. The slow scanner system 3 is arranged for example in the beam path directly upstream of the projection optical unit 2.

The fast scanner system 5 has, depending on the embodiment variant, one or two scanning axes (mirror axes) 51, 52, these preferably being oriented orthogonally with respect to one another. Depending on the embodiment variant, the scanning axes 51, 52, which are also designated as scanning axes, are coupled to a common, tiltable (tip-tilt mode) deflection mirror or to a respective dedicated, separate deflection mirror, which are arranged in a cascaded fashion. The use of a scanner system having two scanning axes 51, 52 and a common tiltable deflection mirror has the advantage that costly intermediate optical units can be saved and the entire construction of the device 1 turns out to be more compact. The fast scanner system 5 deflects the pulsed laser beam L1 from the beam source 6 or the femtosecond laser pulses thereof with a defined scanning movement f in a deflection plane FF oriented perpendicularly to a projection plane $P_{xy}$ corresponding to the plane of the drawing in FIG. 1a. In the projection plane $P_{xy}$ of the fast scanner system 5 illustrated schematically in FIG. 1a, the scanning axis 51 is oriented along the x-axis and the scanning axis 52 is oriented along the y-axis. The movement vector a represents the excursion of the deflection mirror about the scanning axis 52 (y-axis) with an excursion amplitude A in the x-direction, and the movement vector b represents the excursion of the deflection mirror about the scanning axis 51 (x-axis) with an excursion amplitude B in the y-direction. In the case of a synchronized excursion, i.e. one that is at the same frequency ($\omega_x=\omega_y$) and not phase shifted ($\phi=0$), about the two scanning axes 51, 52, the femtosecond laser pulses are deflected with a scanning movement f, which is represented by a corresponding movement vector in FIG. 1a. The excursion amplitudes A, B thus determine the orientation $\theta$ and excursion amplitude F of the resulting scanning movement f of the scanner system 5 in the deflection plane FF perpendicular to the projection plane $P_{xy}$.

The slow scanner system 3 preferably has two scanning axes (mirror axes) which are oriented orthogonally with respect to one another and which are coupled to a common, tiltable deflection mirror or to two separate deflection mirrors.

Preferably, the slow scanner system 3 is embodied as freely addressable in the form of two galvanometer scanners or with a two-axis deflection mirror that is tiltable in the tip-tilt mode (e.g. governed by means of piezoelements). Depending on the operating mode or construction, the fast scanner system 5 is embodied as a resonant, oscillating, or freely addressable scanner. A sinusoidal operating mode allows, particularly in the case of mechanical resonance scanners with oscillating mirrors (also referred to as MEM (micro electromechanical) scanner or with a piezo-drive), higher frequencies and deflection speeds than are possible with galvanometer scanners. Therefore, use is preferably made of oscillating fast scanner systems 5 in the resonant operating mode, since they are particularly advantageous for practical use on account of their high scanning frequencies. Further scanner types, which in some instances allow even higher frequencies, are known from the literature (e.g. AOM (acousto-optic modulator) scanners or EOM (electro-optic modulator)). Preferably, the fast scanner system 5 and the slow scanner system 3 are embodied and operated with orthogonal scanning axes (mirror axes).

The optional filter module 4 is arranged in the beam path preferably between the fast scanner system 5 and the slow scanner system 3. Depending on the embodiment variant, the filter module 4 includes a fixed and/or controllable diaphragm 41, which can also be embodied as a shutter, wherein the shutter is preferably arranged at the laser and disposed directly downstream of the beam source 6. In one embodiment variant, the diaphragm 41 is embodied as a field stop, that is to say arranged in an intermediate image plane, wherein, moreover, depending of the embodiment variant, the field stop is configured as variable and/or asymmetrical.

Figure 4:
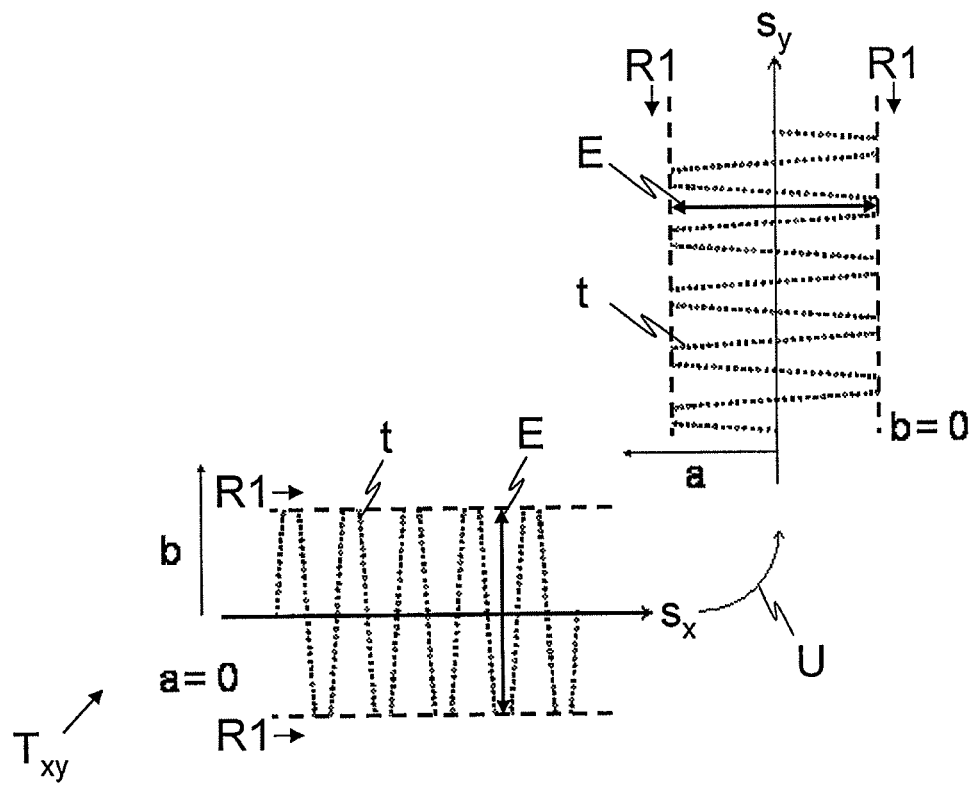
FIG. 4: illustrates the superimposition of a scanning movement of a scanner system onto the processing line with defined alignment of the scanning movement with respect to the processing line and masked-out oscillation peaks of the resulting scanning trajectory.
Figure 5:
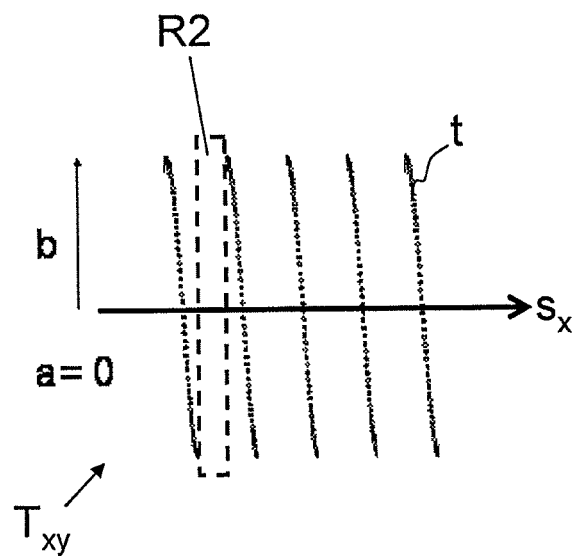
FIG. 5: illustrates the superimposition of a scanning curve of one scanner system onto the processing line of a further scanner system, wherein, in order to produce a straightened scanning pattern, the rising edges of the scanning curve are in each case masked out.

The slow scanner system 3 is designed to scan the eye tissue 8 with the femtosecond laser pulses in an extended processing region along a processing line s. In this case, the slow scanner system 3 deflects the femtosecond laser pulses L2 deflected by the fast scanner system 5 or the femtosecond laser pulses L3, L3* filtered and not masked out by the filter module 4. The direction and shape of the processing line s are determined, as described above with reference to Figure 1a for the fast scanner system 5, by the excursion amplitudes of the excursions about the scanner axes (mirror axes) 31, 32 of the slow scanner system 3. The scanning movement f produced by the fast scanner system 5 is therefore superimposed on the processing line s continuously scanned by the slow scanner system 3, whereby a resulting scanning trajectory t is formed in the processing plane $T_{xy}$, as illustrated in FIG. 1b, with which trajectory the eye tissue 8 is actually processed. FIGS. 2, 4 and 5 illustrate examples of different scanning trajectories t produced for processing the eye tissue 8 on a processing plane $T_{xy}$, which will be discussed in detail later.

The ophthalmological device 1 additionally includes a rotation system for aligning the deflection plane FF with a defined alignment angle with respect to the processing line s, for example perpendicularly ($\pi/2$) or at some other defined angle. The rotation system thus ensures that the scanning movement f is aligned with the processing line s in a defined manner even in the case of changes in direction in processing. The rotation system includes a rotation module 9,9',9" arranged in the optical transmission system 10, in the beam path (L1-L2-L3-L3*-L4) from the beam source 6 to the projection optical unit 2, and serving for performing a defined rotation of the deflection plane FF, and the scanning movement f performed therein, about an optical projection axis z. In various embodiment variants, the rotation module 9 is embodied as a mechanical drive module coupled to the fast scanner system 5 in order to rotate the fast scanner system 5 and hence the deflection plane FF about the optical projection axis z, or the rotation module 9' includes a rotation element configured from prisms or mirrors, for example a rotatable K-mirror, and a drive module, which is coupled to the rotation element and rotates the latter and hence the deflection plane FF about the optical projection axis z, or the function of the rotation module 9" is performed by the fast scanner system 5 or the deflection mirror/mirrors of the fast scanner system 5 that is/are rotatable about the two scanning axes 51, 52. In the embodiment variants in which the rotation module 9, 9' includes a mechanical drive module, the fast scanner system 5 can be used for functions other than the defined alignment of the deflection plane F with respect to the processing line s, for example for producing scanning movements f which are defined by different orientations θ, amplitudes F and, if appropriate, forms, as will be described in greater detail later.

The filter module 4 is designed to mask out certain ones of the femtosecond laser pulses L2 deflected by the fast scanner system 5, in accordance with defined filter criteria. The diaphragm 41 is designed for example in fixed or controllable fashion to mask out femtosecond laser pulses L2 deflected by the fast scanner system 5 into a region outside a defined scanning width E, or to exclude deflected femtosecond laser pulses L2 completely or in a defined region R1, R2 of the scanning curve f In the example in FIG. 4, the filter module 4 is designed to mask out the peaks of the scanning movement f, for example in the case of excursion amplitudes F above a defined amplitude value or scanning width E, in the region R1. In the example in FIG. 5, the filter module 4 is designed to mask out in each case the rising edges of the scanning trajectory t in the region R2, such that a scanning pattern with virtually parallel scanning sections is produced. The masking-out regions R1, R2 are for example dynamically and freely definable and alterable, for example depending on the excursions a, b about the scanning axes 51, 52 and/or on the direction of the processing line s.

The projection optical unit 2 is designed to project the femtosecond laser pulses L4 deflected by the slow scanner system 3 in a focused fashion onto or in the eye tissue 8, wherein the eye tissue 8 is resolved at the focal point Q, depending on the scanning speed or advancing speed in the direction of the processing line s, in each case by an individual femtosecond laser pulse or by a plurality of femtosecond laser pulses projected successively in an overlapping fashion. In one embodiment variant, the projection optical unit 2 is additionally designed to set the focus Q of the focussed, deflected, pulsed laser beam L5, for example by vertical displacements, in the projection direction. Otherwise, the projection optical unit 2 is stationary during the treatment, that is to say that the scanning and processing of the eye tissue 8 does not require any lateral mechanical movement (in the x- and/or y-direction) of lenses of the projection optical unit 2 after the latter has been aligned with the patient's eye for the planned treatment. Fixing to the eye is effected, for example, by means of a vacuum-controlled suction ring.

As can be seen in FIG. 1, the ophthalmological device 1 includes a control module 7, which, depending on the embodiment, is configured as part of the optical transmission system 10 or as a separate unit connected to the optical transmission system 10 via control lines or one or a plurality of data communication connections, for example a plurality of signal and/or data lines and/or a data bus, for control purposes. Depending on the embodiment, the control module 7 is connected to the beam source 6, the fast scanner system 5, the filter module 4, the rotation module 9, 9', 9", the slow scanner system 3 and/or the projection optical unit 2. As is illustrated schematically in FIG. 1, the control module 7 includes a plurality of functional modules, namely a rotation control module 90, a scanning control module 70 and a diaphragm control module 40. The control module 7 preferably includes one or a plurality of processors and an accessible computer-readable data carrier (computer program product), which is connected to the processors in a fixed or removable fashion and on which at least one programmed software module is stored which includes computer program code for controlling the processors. The person skilled in the art will understand that the control module 7 or its functional modules are implemented in different embodiment variants as programmed software modules or else completely or at least partly with hardware components.

The following sections describe the functionality of the control module 7 or its functional modules and the control brought about thereby of the processors and thus of the ophthalmological device 1 with reference to FIGS. 2, 3, 4 and 5.

Depending on the embodiment variant, the control module 7 is designed to control the beam source 6 and/or the projection optical unit 2, for example with regard to pulse energy, pulse frequency or depth of focus, although this will not be described in greater detail in the following sections.

The scanning control module 70 includes, in particular, a fast scanner controller for controlling the fast scanner system 5. The fast scanning controller is designed to control the amplitude F or scanning width of the scanning movement f of the fast scanner system 5. The scanning control module 70 thereby determines the distance between two successive deflected femtosecond laser pulses in the projection plane $P_{xy}$ or the number of femtosecond laser pulses within a defined scanning width E. The fast scanning controller is preferably designed to control the amplitude F or width of the scanning movement f and hence the number of pulses within the scanning width depending on the directional course of the processing line s and/or depending on the current scanning speed of the slow scanner system 3 (or advancing speed in the direction of the processing line s). In the embodiment of the fast scanner system 5 with two scanning axes 51, 52, the fast scanning controller is designed to control the deflection a, b of the femtosecond laser pulses about the scanning axes 51, 52, as indicated in table 1, for performing defined scanning movements f which are defined by different orientations θ, amplitudes F and, if appropriate, shapes (alongside straight scanning movements it is also possible to produce scanning movements f which have shapes with elliptical, Lissajous-shaped, sinusoidal, sawtooth-shaped, trapezium-shaped or rectangular oscillations or other shapes which can be produced by means of Fourier synthesis). In order to deflect the femtosecond laser pulses according to a defined scanning movement f, the control module 7 uses corresponding control parameters for controlling the fast scanner system 5 which are assigned to the relevant scanning movement f designated by an identifier. The excursions about the scanning axes 51, 52 are determined, in particular, with parameters for controlling the respective excursion amplitudes A, B, excursion frequency $\omega_x$, $\omega_y$, and/or relative phase φ (phase shift) between the excursions a, b (oscillation) about the scanning axes 51, 52.

designed, for example, to control the deflection about the scanning axes 31, 32 in accordance with defined processing lines s which are defined by different processing patterns and have, for example, an assigned unique pattern or line identifier. In order to deflect the femtosecond laser pulses onto a processing line s defined, for example, by a stored processing pattern or a time function, the control module 7 uses corresponding control parameters for controlling the slow scanner system 3 which are assigned to the relevant processing line s.

The rotation control module 90 is part of the rotation system and is designed to define and control the rotation of the deflection plane FF or of the scanning movement f by the rotation module 9, 9', 9" on the basis of the directional course of the processing line s. That is to say that the rotation control module 90 and the scanning control module 70, in particular the slow scanner controller, perform a coupled control of the slow scanner system 3 and of the rotation module 9, 9', 9" in order to define and control the processing line s and, in a manner dependent thereon, to determine and control the orientation θ of the deflection plane FF and hence of the scanning movement f Depending on the embodiment variant of the rotation module 9, 9', 9", the rotation control module 90 supplies control signals—dependent on the current direction of the processing line s—for the rotation module 9, 9', 9" to the drive module, the rotation element and/or the fast scanner system 5 (or the fast scanner controller) in order to rotate the deflection plane FF about the optical projection axis z such that it has a defined alignment angle with respect to the processing line s, for example π/2 or some other defined angle.

The embodiment variant in which the function of the rotation module 9" is performed by the fast scanner system 5 or the deflection mirror/mirrors of the fast scanner system 5 that is/are rotatable about the two scanning axes 51, 52 has the advantage that no additional drive elements and/or rotation elements have to be included in the device 1. In this case, the rotation control module 90 can be integrated into the fast scanner controller or control the fast scanner system 5 by means of function calls of the fast scanner controller.

FIG. 2 shows an example of a scanning trajectory t in which the superimposed scanning movement f is adapted to a

TABLE 1

| | | | Control parameter | | | | | |
|---|---|---|---|---|---|---|---|---|
| | Scanning movement | | | Excursion about first scanning axis | | Excursion about second scanning axis | | Phase |
| Identifier | Shape | Orientation | Amplitude | Amplitude | Frequency | Amplitude | Frequency | shift |
| ... | ... | ... | ... | ... | ... | ... | ... | ... |

Figure 3:
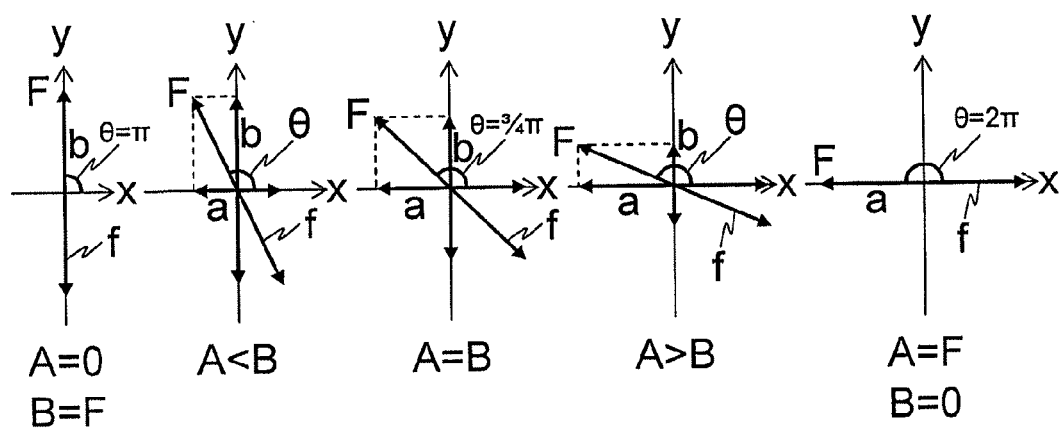
FIG. 3: illustrates a sequence of intermediate stages when continuously increasing or decreasing the excursion amplitudes of the deflections about two mirror or scanning axes aligned orthogonally with respect to one another, for dynamically adapting the alignment of the scanning movement to a change in the direction of the processing line.

FIG. 1a illustrates an example of how, by the control of the excursion amplitudes A, B about the scanning axes 51, 52, the orientation θ and excursion amplitude F of the resulting scanning movement f on the projection plane $P_{xy}$ can be set by the scanning control module 70 if the remaining control parameters are set in such a way that the deflection a, b about the two scanning axes 51, 52 is effected with the same frequency $\omega_x = \omega_y$ and without a phase shift φ=0 between the excursion oscillations (a more detailed description is given later with reference to FIG. 3).

The scanning control module 70 additionally includes a slow scanner controller for controlling the deflection of the femtosecond laser pulses about the scanning axes 31, 32 of the slow scanner system 3. The slow scanner controller is change in the direction of the processing line $s_x$, $s_y$, for example from the x-direction to the y-direction. As is illustrated schematically in FIG. 2, the rotation control module 90 is designed to control the fast scanner system 5 in such a way that it sets the excursion amplitude B of the excursion b in the y-direction about the scanning axis 51 and the excursion amplitude A of the excursion a in the x-direction about the scanning axis 52 depending on the direction of the processing line $s_x$, $s_y$, for example in such a way that, during the processing by the slow scanner system 3 along the processing line s, in the x-direction, the excursion amplitude B of the fast scanner system 5 is set to a defined scanning width E and the excursion amplitude A of the fast scanner system 5 is set to zero, and, conversely, during the processing by the slow scanner system 3 along the processing line $s_y$ in the y-direction, the excursion amplitude A of the fast scanner system 5 is set to the defined scanning width F and the excursion amplitude B is set to zero. In the transition region U from processing in the x-direction to processing in the y-direction, the excursion amplitudes A, B of the excursions a, b of the fast scanner system 5 are continuously increased and reduced, respectively, for example.

FIG. 3 illustrates a sequence of a plurality of intermediate stages in the control of the excursions a, b about the scanning axes 51, 52 for adapting the orientation θ of the scanning movement f of θ=π/2 to π=π to the change in direction of π/2 of the processing line $s_x$, $s_y$ in the transition region U from the x-direction to the y-direction (in an operating mode with a relative phase φ=π) As can be seen in FIG. 3, in this case the excursion amplitude A of the excursion a (in the x-direction) about the scanning axis 52 (y-axis) is increased continuously from A=0 through A<B, A=B and A>B to A=F, whereas the excursion amplitude B of the excursion b (in the y-direction) about the scanning axis 51 (x-axis) is reduced continuously from B=F through B>A, B=A and B<A to B=0.

In FIGS. 2, 4, 5, the circles in each case schematically represent the focus midpoints of a pulsed laser beam (processing beam L5) or of a femtosecond laser pulse at the focus Q. The scanning trajectories t illustrated in FIG. 42 have laser pulses distributed non-uniformly in specific regions. As a measure against that, depending on the embodiment variant and/or application, the laser beam or the laser pulses are masked out by the filter module 4 outside a defined transmission region or in a specific masking-out region, for example by means of a shutter and/or a diaphragm 41, as a result of which selectively determined regions of the scanning trajectory t are selected.

The diaphragm control module 40 is designed to control the controllable, variable diaphragm region or transmission region of the diaphragm 41 in the filter module 4. The diaphragm control module 40 is designed, for example, to control the size of the variable diaphragm region or transmission region depending on the scanning speed of the slow scanner system 3.

In the example in FIG. 4, by way of example, optionally the oscillation peaks, which have comparatively more densely successive laser pulses, in the regions R1 lying outside the defined scanning width E are masked out by the filter module 4, preferably by a diagram 41, in particular field stop.

In the example in FIG. 5, the rising edges of the scanning trajectory t in the region R2 are in each case masked out, such that selectively only the falling branches of the scanning trajectory t are used for processing, in which case, by way of example, in addition as in FIG. 4, the oscillation peaks in the region R1 are also cut off. In order to mask out the region R2 in the scanning trajectory, the diaphragm control module 40 controls the variable diaphragm region of the diaphragm 41 such that the corresponding femtosecond laser pulses are masked out in the region R2 in the superimposed scanning movement f in each case for rising edges, but are transmitted again for falling edges, that is to say that the diaphragm region R2 changes in a manner synchronized with the oscillation of the scanning movement f between masking-out mode and transmission mode. Preferably, the region R2 is masked out by a shutter that is arranged at the laser and disposed downstream of the beam source 6 and is closed for masking out the region R2 and is otherwise open.

In order to match the pulse separation within a branch or an edge, in a further embodiment variant, by means of the control module 7, the pulse frequency will be adapted depending on the position in the scanning trajectory t (e.g. by means of pulse pickers) or the excursion amplitude A, B of the fast scanner system 5 is altered dynamically. The scanning control module 70 is designed, for example, to control the excursion amplitude F of the fast scanner system 5 depending on the directional course of the processing line s and/or depending on the current scanning speed of the slow scanner system 3. By virtue of the resulting dynamic increase (expansion) or decrease (compression), respectively, in the excursion amplitude F of the scanning curve f, the distance between successive individual femtosecond laser pulses on the scanning movement f or scanning trajectory t can be increased or decreased, respectively, and the number of laser pulses in the transmission region within the scanning width E not masked out, can thereby be controlled in a variable manner.

Finally, it should be mentioned that although the computer program code was assigned to specific functional modules in the description, the person skilled in the art will understand that the computer program code can be changed in a variously structured fashion, without departing from the protected subject matter.

What is claimed is:

1. An ophthalmological device for processing eye tissue using femtosecond laser pulses comprising:
   a projection optical unit for the focused projection of the femtosecond laser pulses into the eye tissue,
   a first beam-deflecting scanner system, disposed upstream of the projection optical unit, said upstream direction being defined extending from the projection optical unit and toward a source of the femtosecond laser pulses, for scanning the eye tissue with the femtosecond laser pulses along a processing line,
   a second beam-deflecting scanner system, disposed upstream of the first beam-deflecting scanner system, for scanning the eye tissue with the femtosecond laser pulses in a scanning movement (f) superimposed on the processing line, and running in a deflection plane (FF), and
   a rotation system for aligning the deflection plane (FF) with a defined angle with respect to the processing line, wherein the rotation system comprises a rotation module and a rotation control module, the rotation module being configured to perform a defined rotation of the deflection plane (FF) about an optical projection axis (z), and the rotation control module being configured to define the rotation of the deflection plane (FF) on the basis of the course of the processing line.

2. The device according to claim 1, wherein the first beam-deflecting scanner system comprises two scanning axes aligned orthogonally with respect to one another for deflecting the femtosecond laser pulses, the second beam-deflecting scanner system configured to deflect the femtosecond laser pulses with a scanning speed that is a multiple of the scanning speed of the first beam-deflecting scanner system, and wherein the rotation system is disposed upstream of the first beam-deflecting scanner system.

3. The device according to claim 1, wherein the rotation module further comprises one of a rotation element configured from mirrors, a rotation element configured from prisms, and a drive module coupled to the second beam-deflecting scanner system and configured to rotate the second beam-deflecting scanner system about the optical projection axis (z).

4. The device according to claim 1, wherein the second beam-deflecting scanner system has two scanning axes aligned orthogonally with respect to one another for deflecting the femtosecond laser pulses, and wherein the rotation control module is configured to determine the alignment of the scanning movement (f) running in the deflection plane (FF) with respect to the processing line by coupled control of the excursion amplitude (B) of the deflection (b) about the first scanning axis and of the excursion amplitude (A) of the deflection (a) about the second scanning axis.

5. The device according to claim 1, further comprises a scanning control module, configured to control a width (F) of the scanning movement (f) of the second beam-deflecting scanner system depending on at least one of directional course of the processing line and current scanning speed of the first beam-deflecting scanner system.

6. The device according to any of claim 1, further comprising a diaphragm arranged between the first beam-deflecting scanner system and the second beam-deflecting scanner system and serving for masking out femtosecond laser pulses that are deflected by the upstream second beam-deflecting scanner system into a region (R1) outside a defined transmission region (E).

7. The device according to claim 6, further comprising a scanning control module, which is configured to control a width (F) of the scanning movement (f) of the second beam-deflecting scanner system in such a way that the distance between two successive femtosecond laser pulses and the number of femtosecond laser pulses in the transmission region (E) are variable.

8. The device according to claim 6, wherein the diaphragm has a controllable, variable diaphragm region or transmission region.

9. The device according to claim 8, further comprising a diaphragm control module which is configured to control a size of the variable diaphragm region or transmission region depending on a scanning speed of the first beam-deflecting scanner system.

10. The device according to claim 6, wherein the diaphragm is configured as a field stop.

11. The device according to claim 1, wherein the first beam-deflecting scanner system has a significantly greater degree of excursion in comparison with the second beam-deflecting scanner system.

12. The device according to claim 2, wherein the two scanning axes of the first beam-deflecting scanner system that are aligned orthogonally with respect to one another are coupled to a common deflection mirror.

13. The device according to claim 1, wherein the second beam-deflecting scanner system is configured to scan the eye tissue with the femtosecond laser pulses in an oscillating scanning movement (f).

14. The device according to claim 1, further comprising a controllable filter module for selectively excluding femtosecond laser pulses in a defined region (R2) of the superimposed scanning movement (f).

15. An ophthalmological device for processing eye tissue using femtosecond laser pulses comprising:
  a projection optical unit for the focused projection of the femtosecond laser pulses into the eye tissue,
  a first beam-deflecting scanner system, disposed upstream of the projection optical unit, said upstream direction being defined extending from the projection optical unit and toward a source of the femtosecond laser pulses, for scanning the eye tissue with the femtosecond laser pulses along a processing line,
  a second beam-deflecting scanner system, disposed upstream of the first beam-deflecting scanner system, for scanning the eye tissue with the femtosecond laser pulses in a scanning movement (f) superimposed on the processing line, and running in a deflection plane (FF),
  a rotation system for aligning the deflection plane (FF) with a defined angle with respect to the processing line, and
  a scanning control module, configured to control a width (F) of the scanning movement (f) of the second beam-deflecting scanner system depending on at least one of directional course of the processing line and current scanning speed of the first beam-deflecting scanner system.

16. An ophthalmological device for processing eye tissue using femtosecond laser pulses comprising:
  a projection optical unit for the focused projection of the femtosecond laser pulses into the eye tissue,
  a first beam-deflecting scanner system, disposed upstream of the projection optical unit, said upstream direction being defined extending from the projection optical unit and toward a source of the femtosecond laser pulses, for scanning the eye tissue with the femtosecond laser pulses along a processing line,
  a second beam-deflecting scanner system, disposed upstream of the first beam-deflecting scanner system, for scanning the eye tissue with the femtosecond laser pulses in a scanning movement (f) superimposed on the processing line, and running in a deflection plane (FF),
  a rotation system for aligning the deflection plane (FF) with a defined angle with respect to the processing line, and
  a diaphragm arranged between the first beam-deflecting scanner system and the second beam-deflecting scanner system and serving for masking out femtosecond laser pulses that are deflected by the upstream second beam-deflecting scanner system into a region (R1) outside a defined transmission region (E).

17. An ophthalmological device for processing eye tissue using femtosecond laser pulses comprising:
  a projection optical unit for the focused projection of the femtosecond laser pulses into the eye tissue,
  a first beam-deflecting scanner system, disposed upstream of the projection optical unit, said upstream direction being defined extending from the projection optical unit and toward a source of the femtosecond laser pulses, for scanning the eye tissue with the femtosecond laser pulses along a processing line,
  a second beam-deflecting scanner system, disposed upstream of the first beam-deflecting scanner system, for scanning the eye tissue with the femtosecond laser pulses in a scanning movement (f) superimposed on the processing line, and running in a deflection plane (FF), and
  a rotation system for aligning the deflection plane (FF) with a defined angle with respect to the processing line,
  wherein the first beam-deflecting scanner system has a significantly greater degree of excursion in comparison with the second beam-deflecting scanner system.

18. An ophthalmological device for processing eye tissue using femtosecond laser pulses comprising:
  a projection optical unit for the focused projection of the femtosecond laser pulses into the eye tissue,
  a first beam-deflecting scanner system, disposed upstream of the projection optical unit, said upstream direction being defined extending from the projection optical unit and toward a source of the femtosecond laser pulses, for scanning the eye tissue with the femtosecond laser pulses along a processing line,
  a second beam-deflecting scanner system, disposed upstream of the first beam-deflecting scanner system, for scanning the eye tissue with the femtosecond laser pulses in a scanning movement (f) superimposed on the processing line, and running in a deflection plane (FF), a rotation system for aligning the deflection plane (FF) with a defined angle with respect to the processing line, and a controllable filter module for selectively excluding femtosecond laser pulses in a defined region (R2) of the superimposed scanning movement (f).

* * * * *